(12) United States Patent
Schleipen et al.

(10) Patent No.: US 8,520,211 B2
(45) Date of Patent: Aug. 27, 2013

(54) CARRIER FOR OPTICAL DETECTION IN SMALL SAMPLE VOLUMES

(75) Inventors: Johannes Joseph Hubertina Barbara Schleipen, Eindhoven (NL); Toon Hendrikus Evers, Eindhoven (NL); Jeroen Hans Nieuwenhuis, Waalre (NL); Wendy Uyen Dittmer, Eindhoven (NL); Dominique Maria Bruls, Eindhoven (NL); Menno Willem Jose Prins, Rosmalen (NL); Jacobus Hermanus Maria Neijzen, Heeze (NL); Yannyk Parulian Julian Bourquin, Les Acacias (CH)

(73) Assignee: Koninklijke Philips N.V., Eindhoven (NL)

(*) Notice: Subject to any disclaimer, the term of this patent is extended or adjusted under 35 U.S.C. 154(b) by 418 days.

(21) Appl. No.: 12/935,947

(22) PCT Filed: Apr. 7, 2009

(86) PCT No.: PCT/IB2009/051454
§ 371 (c)(1),
(2), (4) Date: Oct. 1, 2010

(87) PCT Pub. No.: WO2009/125339
PCT Pub. Date: Oct. 15, 2009

(65) Prior Publication Data
US 2011/0026030 A1 Feb. 3, 2011

(30) Foreign Application Priority Data
Apr. 9, 2008 (EP) .................................. 08103454

(51) Int. Cl.
*G01N 21/00* (2006.01)

(52) U.S. Cl.
USPC ......................................................... 356/442

(58) Field of Classification Search
USPC ......... 356/300–334, 445–446, 417, 432–436, 356/440–442
See application file for complete search history.

(56) References Cited

U.S. PATENT DOCUMENTS

| 5,110,205 A | 5/1992 | Suzuki et al. |
| 2002/0022276 A1 | 2/2002 | Zhou et al. |
| 2003/0015428 A1 | 1/2003 | Becker et al. |

(Continued)

FOREIGN PATENT DOCUMENTS

| WO | 9316383 A1 | 8/1993 |
| WO | 2004113886 A1 | 12/2004 |
| WO | 2005111614 A1 | 11/2005 |
| WO | 2006134569 A2 | 12/2006 |

OTHER PUBLICATIONS

Lee et al: "Manipulation of Biological Cells Sing a Microelectromagnet Matrix"; Applied Physics Letters, vol. 85, No. 6, Aug. 2004, pp. 1063-1065.

*Primary Examiner* — Gregory J Toatley
*Assistant Examiner* — Dominic J Bologna

(57) ABSTRACT

A carrier and an apparatus for optical detection of a sample in a sample chamber includes en optical structure for refracting an input light beam into the adjacent sample chamber and for collecting an output light beam from light that originates in the sample chamber from the input light beam. The optical structure includes grooves in the surface of the carrier in which the Input light beam is transmitted Over a short distance through a sample. The optical structure can also be used for a wetting detection.

17 Claims, 9 Drawing Sheets

(56) References Cited

U.S. PATENT DOCUMENTS

| | | |
|---|---|---|
| 2004/0201835 A1* | 10/2004 | Coates et al. ............. 356/73 |
| 2005/0007596 A1* | 1/2005 | Wilks et al. ............. 356/436 |
| 2005/0048599 A1* | 3/2005 | Goldberg et al. ............. 435/34 |
| 2005/0110989 A1* | 5/2005 | Schermer et al. ............. 356/246 |
| 2006/0008924 A1* | 1/2006 | Anker et al. ............. 436/526 |
| 2007/0146717 A1* | 6/2007 | Prins et al. ............. 356/445 |

\* cited by examiner

CARRIER FOR OPTICAL DETECTION IN SMALL SAMPLE VOLUMES

The invention relates to a carrier and to an apparatus for detection in a sample in a sample chamber. Moreover, it relates to the use of such a carrier and such a device and to a method for the detection of magnetic particles.

The US 2005/0048599 A1 discloses a method for the investigation of microorganisms that are tagged with particles such that a (e.g. magnetic) force can be exerted on them. In one embodiment of this method, a light beam is directed through a transparent material to an optical interface, defined by the transition from the transparent medium to another, optically less dense material, where it is totally internally reflected. Light of this beam that penetrates the optically less dense medium as an evanescent wave is scattered by microorganisms, molecules and/or other components at the optical interface and then detected by a photodetector or used to illuminate the microorganisms for visual observation.

Based on this situation it was an object of the present invention to provide means for optical detections in a sample, wherein it is desirable that the detection can be restricted to small volumes, preferably volumes with an extension between 1 and 1000 µm.

The carrier according to the present invention is intended for optical detection in a sample in an adjacent sample chamber, i.e. in the space exterior to the carrier. In this context, the term "detection" may comprise any kind of interaction of light with a sample. The detection may preferably comprise the qualitative or quantitative detection of target components comprising label particles, wherein the target components may for example be biological substances like biomolecules, complexes, cell fractions or cells. The carrier will usually be made at least partially from a transparent material, for example glass or polystyrene, to allow the propagation of light of a given (particularly visible, UV, and/or IR) spectrum. It comprises on its surface an optical structure that can refract an input light beam, which impinges on said structure from the interior of the carrier, into the adjacent exterior space, i.e. into the sample chamber. Moreover, the optical structure shall be able to collect an output light beam impinging on it from the exterior space, i.e. from the sample chamber, which comprises light originating from the input light beam. This collection of the output light beam shall be possible simultaneously to the refraction of the input light beam, i.e. under the same operating conditions. Photons of the input light beam may directly pass over to the output light beam; they may however also be converted in some way, e.g. by absorption and re-emission, stimulated emission, or scattering, before they contribute to the output light beam.

Due to the twofold refraction of light at the optical interface, the light is redirected in a direction where it originally came from. A major advantage of this geometry is that the detection of light can be done from the same side as the illumination, i.e. the detection of light is not hindered by any structures that are placed on top of the carrier (e.g. the finite thickness of the sample fluid itself or a cover plate needed for controlling the fluid flow over the carrier substrate).

Besides recollecting the twofold refracted light beam for detection, it is equally well possible to use the optical structure only for excitation of a shallow volume on top of the carrier substrate, and to do the detection with other detection means in a direction other than the refracted light beam (e.g. using dark-field detection of scattered or photoluminescent light originating from the probed volume that is excited using the optical structure, for instance using a microscope that is looking in a direction perpendicular to the carrier substrate, either from the bottom, or from the top side of the substrate).

The described carrier has the advantage to provide a surface structure which can emit input light into an adjacent sample and simultaneously re-collect that light after its interaction with the sample. It should be noted in this context that the input light is actually emitted (refracted) into the sample chamber and can propagate there over arbitrary distances, depending on the actual refractive geometry of the claimed carrier substrate. It can therefore cover a larger volume than evanescent waves that are generated during a total internal reflection of a light beam and that decay exponentially over very short distances in the order tens of nanometers. The volumes that are probed by the emitted light beam are nevertheless still on a microscopic scale, because re-collection of input light takes place in the surface structure itself.

The exact height of the manipulation or probe volume depends on the size of the particles that are embedded in this volume. The invention allows particularly to probe only a monolayer of molecules or particles that are bio-chemically bound to the surface. As such, the height of the probe volume is in the order of the diameter of the particles that need to be probed. A higher probe volume would lead to undesired detection of particles present in the optically less dense medium, that are not bio-chemically bound to the surface. Higher probe volumes would be allowed, however, if non-bound particles are removed prior to detection by a (e.g. magnetic) washing step.

The invention further relates to an apparatus for optical detection in a sample in a sample chamber, comprising:

a) A carrier of the kind described above, i.e. with an optical structure on its surface that can refract an input light beam into an adjacent sample chamber and that can simultaneously collect an output light beam from said sample chamber.

b) A light source for emitting an input light beam through the carrier towards the optical structure of the carrier. The light source may for example be a laser or a light emitting diode (LED), optionally provided with some optics for shaping and directing the input light beam.

The apparatus comprises as an essential component a carrier of the kind described above. Reference is therefore made to the description of this carrier for more information on the details and advantages of said microelectronic sensor device.

It was already mentioned that it is an advantage of the invention to provide means for the investigation of limited, small volumes of a sample, close to an interface where e.g. a biochemical reaction can take place. In preferred embodiments, the light that is collected as the output light beam by the optical structure on the carrier has passed a distance of less than 1000 µm, preferably less than 100 µm, most preferably less than 10 µm through the exterior space of the carrier, i.e. through the sample chamber. Thus the output light beam will comprise information about events that happened in a small volume of typically some fractions of a micro liter adjacent to the optical structure. The preferred height of the probe volume depends on the particles (molecules, macroscopic labels) that are being probed. For macroscopic detection labels (such as magnetic or fluorescent-magnetic beads with a typical diameter of 100 . . . 2000 nm), the height of the probe volume is typically 1 to 10 times the diameter of the probed particles.

In a preferred embodiment of the invention, the optical structure of the carrier comprises at least one facet, which will be called "excitation facet" in the following, via which light of an input light beam can be emitted into the adjacent sample chamber, and at least one corresponding facet, called "collection facet" in the following, via which the emitted light can be re-collected (as far as it could propagate undisturbed through the sample chamber). In this design, the space between the excitation facet and the collection facet constitutes the volume that is probed by the input light beam. Processes like absorption or scattering that take place in this volume will affect the amount and/or spectrum of light of the input light beam which can be re-collected at the collection facet. Said amount/spectrum therefore comprises information about such events and the substances causing them. In another configuration, e.g. using dark field detection in a direction perpendicular to the carrier, scattered and/or fluorescent light may be collected from the probe volume using both the excitation and collection facets.

The output light beam can optionally comprise light from a photoluminescence (i.e. fluorescence and/or phosphorescence) that was stimulated in a sample in the sample chamber by the input light beam. In this case the optical structure is preferably designed such that only a limited (small) sub-volume of the sample chamber is excited by the input light beam and/or that only photoluminescence light from such a limited volume is collected into the output light beam. The output light beam may optionally comprise additional light that stems directly from the input light beam.

An optical structure with the desired features can be designed in several different ways. In a preferred embodiment, the optical structure comprises at least one hole or groove in the surface of the carrier (wherein the material of the carrier shall be transparent in this region). Instead of describing such an optical structure by hole or grooves, one could of course equivalently characterize it with corresponding crests, ridges or the like. The part of the surface of the hole/groove that is illuminated by the input light beam will act as an excitation facet via which input light is refracted into the adjacent sample chamber; the residual surface of the hole/groove typically will act as a collection facet via which light originating in the sample chamber is collected. If the transmission of the input light beam through the sample chamber shall be observed, the collection facet will usually be arranged oppositely to the excitation facet. In this design of the optical structure, it will typically be the volume inside the hole or groove that is manipulated by the input light beam. The size of this volume can therefore arbitrarily be adapted by choosing corresponding dimensions of the hole/groove. The holes/grooves may particularly be triangular or trapezoidal prism-like structures.

The aforementioned hole or groove has preferably a depth between about 0.01 µm and 1000 µm, preferably between 0.1 µm and 2 µm. These dimensions are for example suited for the investigation of magnetically interactive beads as they are often used in biosensors for labeling target components and for allowing their manipulation with magnetic forces.

The hole or groove in the surface of the carrier preferably has a cross section with two oppositely slanted, opposing facets. Such a cross-section may particularly be realized by a triangular or trapezoidal cross section. Light emitted by one of the facets can then be re-collected by the opposing facet.

While the above embodiments comprise the case that only one single hole or groove is present, the optical structure will preferably have a plurality of such holes or grooves that are arranged in a regular or irregular pattern. The dimensions of the single holes/grooves then determine the extension of the optically manipulated sample volume in a direction vertical to the surface of the carrier, while the size of the pattern of all holes/grooves determines the extension of this sample volume in directions parallel to the carrier surface. Moreover, it is possible that all holes/grooves have the same shape, or that they have different shapes. In the latter case, it is preferred that the shape (e.g. described by the inclination of the groove-facets) varies in a continuous way in one or two direction(s) along the surface of the carrier, thus providing a quasi-continuum of optical conditions on the surface.

The carrier may optionally comprise a contact surface with a plurality of isolated investigation regions that have the described optical structure. Detection in a sample with the optical structures can then take place simultaneously in several distinct investigation regions.

According to a further development of the invention, the optical structure is coated with binding sites for target components of the sample. Such binding sites may for example be biological molecules that specifically bind to particular molecules in a sample.

In a preferred embodiment of the invention, the apparatus comprises a magnetic field generator for generating a magnetic field in the sample chamber. Via such magnetic field it is possible to exert forces on magnetic particles (e.g. beads) and to move them in a desired way. The generated magnetic field may particularly be temporarily modulated in a predetermined way, for instance such that it yields a rotating magnetic field in the sample chamber. Magnetic particles with non-spherical properties will then move corresponding to the modulated field, e.g. rotate, which can be detected as a characteristic modulation of the sensor signals.

According to another embodiment, the aforementioned magnetic field may be substantially parallel to the surface of the carrier. Chains or pillars of a plurality of magnetic particles that are often formed under the influence of an external magnetic field will then be oriented parallel to the surface of the carrier. In this way the signal of a single magnetic particle that is bound to the carrier surface can be enhanced by the further magnetic particles that are magnetically linked to it in the mentioned chain. Especially for low concentrations of bound magnetic particles, this process can considerably increase the sensitivity of the detection.

The effect of the optical structure to refract an input light beam into an adjacent sample chamber requires that appropriate optical conditions prevail, i.e. that the refractive indices of the carrier and the adjacent sample as well as the angle of incidence of the input light beam lie in appropriate ranges where refraction can occur. The angle of incidence and the refractive index of the carrier can be fixed by the design of the apparatus; the refractive index of the sample will however change in the applications of the apparatus depending on the sample material that is manipulated. The resulting dependence of the behavior of the apparatus on the refractive index of the sample material can be exploited to gain information about the material in the sample chamber. To this end it is possible to design the apparatus (mainly by selecting the angle of incidence of the input light beam with respect to the surface normal to the facet of refraction, and the refractive index of the carrier) in such a way that:

a) At least a part of the input light beam is refracted into the sample chamber (as assumed in the embodiments described above) if the sample chamber comprises a medium with a refractive index lying in a first given interval.

b) Said part of the input light beam is not refracted into the sample chamber but totally internally reflected by the optical structure if the sample chamber comprises a medium with a refractive index lying in a second interval (different from the first interval).

It should be noted that the aforementioned conditions a) and b) may prevail at a given position or in a given sub-area of the optical structure only or for the complete optical structure.

The observed effects on the input light beam, i.e. either its refraction into the sample chamber or its total internal reflection, allow a conclusion on the refractive index of the material in the sample chamber, i.e. on the material itself.

A particularly important application of this approach is that of a wetting detection in which a distinction is made if the contact surface and the optical structure are properly contacted by a liquid sample or if they are dry (i.e. in contact with air filling the whole sample chamber or with gas bubbles preventing a contact of the sample to the contact surface). Furthermore, this wetting sensor can give information on the filling speed of a measuring volume/chamber, which can e.g. give information about viscosity, temperature etc.

The apparatus may optionally further comprise a light detector for detecting a characteristic parameter of light originating from the input light beam, particularly a characteristic parameter of the output light beam. The light detector may comprise any suitable sensor or plurality of sensors by which light of a given spectrum can be detected, for example a 1D or 2D detector array, single-spot or multiple-spot photodiodes, photo resistors, photocells, a CCD or CMOS chip, or a photo multiplier tube. The light that is detected by the light detector may particularly be input light that never entered into the sample chamber, for example because it was totally internally reflected at the optical structure; it may be input light that entered the sample chamber by refraction but that was not recollected by the optical structure; it may be light of photoluminescence (i.e. fluorescence and/or phosphorescence) excited by the input light beam in the sample chamber that thereafter propagated through the carrier or not; or it may be light of the output light beam that (by definition) originates from the input light beam and was collected by the optical structure. Moreover, the detected characteristic parameter may particularly be the intensity or an image of the intensity profile of the output light beam.

The characteristic parameter that is determined by the light detector may particularly comprise the amount of the detected light (e.g. expressed as the intensity of the light beam within a given cross section). Another important example of a characteristic parameter is the propagation direction of the detected light. Still another example is a boundary on the optical structure that separates areas with different optical effects on the input light beam, e.g. an area where total internal reflection occurs from an area of "normal" reflection.

The optical structure of the carrier may have spatially homogenous optical properties, e.g. realized by a regular, periodic pattern of identical grooves or holes. It may however also have locally varying optical properties, for example a varying shape (inclination, depth, pitch etc.) of the grooves/holes that constitute the structure. The properties may particularly relate to the total internal reflection of an incident input light beam. In this case the boundary that separates an area on the optical structure where total internal reflection occurs from an area of "normal" reflection will have different courses for media with different refractive indices in the sample chamber. The boundary will therefore implicitly provide information about the refractive index of said media.

The light detector may optionally be adapted to separately detect components of the output light beam that differ in the number of times they were refracted and/or reflected by the carrier. The output light beam may for example comprise a primary component that propagated through the carrier without further interactions (besides a possible refraction when leaving the carrier) with interfaces after it was collected by the optical structure, and it may further comprise a secondary component of light that was totally internally reflected by the optical structure after its collection by said structure. The characteristic parameters of these components of the output light beam will typically contain information about the conditions in the sample chamber, for example the refractive index of the sample. To be able to separately detect different components of the output light beam, the light detector may comprise physically distinct subunits, for example two photodiodes disposed at different locations, and/or it may be moved to pick up measurements at different locations, thus resolving the components of the output light beam in the temporal range.

According to a further development of the embodiment with a light detector, the apparatus further comprises an evaluation unit for evaluating the detection signal provided by the light detector with respect to the presence and/or amount of a target component in the sample chamber. An increasing concentration of particles in a sample may for example lead to more scattering of input light after its refraction into the sample chamber and thus to a decreasing intensity of the twofold-refracted output light beam. An increasing concentration of a photoluminescent substance, on the contrary, will lead to an increasing amount of photoluminescence light, whether this is observed in the twofold-refracted output light beam, or in the light detected in dark-field configuration in a direction perpendicular to the carrier surface. In any case, the detected light will carry information about the presence and amount of a target component one is interested in.

Additionally to a light detector, the apparatus may further comprise an evaluation unit for evaluating the detection signal of the light detector with respect to a distinction between two different media that may be present in the sample chamber and/or with respect to the refractive index of the medium in the sample chamber. This approach is based on the fact that the medium in the sample chamber affects (e.g. via its color or particularly its refractive index) if and how the input light beam propagates into the sample and, consequently, affects the characteristics of the resulting output light beam. This dependency can be exploited by the evaluation unit for differentiating between possible media in the sample chamber, particularly between air and liquid when operating as a wetting detector. As many effects of the medium in the sample chamber continuously depend on its refractive index, quantitative measurements will even be possible that allow to infer the value of this index.

According to a further aspect, the invention relates to an apparatus for detection of magnetic particles in a sample that is provided in a sample chamber, said apparatus comprising the following components:

a) A carrier with a surface that is adjacent to the sample chamber and at which the magnetic particles can be detected.

b) A magnetic field generator for generating a magnetic field in the sample chamber that is substantially parallel to the surface of the carrier and for simultaneously exerting a magnetic force on magnetic particles in the sample chamber that pulls them away from said surface. Typically, the magnetic force will be generated by a gradient of the magnetic field that is directed away from the surface.

The aforementioned apparatus may particularly be an apparatus of the kind described above, i.e. its carrier may have an optical structure on the surface that can reflect an input light beam into the adjacent sample chamber and that can simultaneously collect an output light beam impinging on it from the sample chamber, wherein said output light beam comprises light originating from the input light beam. Furthermore, the apparatus will usually comprise a light source for emitting the input light beam through the carrier towards the surface of said carrier. Due to this relationship to the apparatus described above, reference can be made to the above description for more information on the details, advantages and modifications of the present apparatus. It should however be noted that other particular embodiments of the present apparatus are possible, too. Thus it is for example possible that an input light beam is totally internally reflected at a (smooth) surface of the carrier to yield a detectable output light beam, and that particles at the surface are detected because they disturb said total internal reflection (giving rise to "Frustrated Total Internal Reflection", FTIR). Moreover, the magnetic particles may be detected by optical, mechanical, acoustics, magnetic or any other suitable procedure.

Independent of the method by which magnetic particles at the surface of the carrier are detected, the apparatus of the further aspect has the advantage that magnetic particles at the surface are subjected both to a magnetic field that is parallel to the surface and to forces that pull them away from the surface. Thus unbound magnetic particles can be removed from the surface, leaving only the bound magnetic particles one is interested in. Besides this, also magnetic particles that are attached to bound magnetic particles via a magnetic coupling may be left at the surface, wherein the corresponding chains or pillars of magnetic particles become oriented parallel to the surface. All magnetic particles of these chains will hence be in a volume close to the surface where they can be detected. In this way a plurality of magnetic particles becomes associated with a (single) binding event at the surface of the carrier, thus enhancing the signals that are derived from such a binding event accordingly.

The sample chamber of the above apparatuses will often have an elongated shape with long and short sides and some axial extension parallel to the long sides. This is for example the case if the sample chamber is a fluidic channel through which a liquid sample can flow in a controlled way. According to a preferred embodiment of the invention, an apparatus with such an elongated sample chamber comprises at least one magnetic field generator the poles (North and South) of which are disposed on opposite long sides of the sample chamber. In this way very uniform magnetic conditions can be established in a large region comprising the axial extension of the sample chamber.

The invention further relates to the use of the carrier and the apparatus described above for molecular diagnostics, biological sample analysis, or chemical sample analysis, food analysis, and/or forensic analysis. Molecular diagnostics may for example be accomplished with the help of magnetic beads or photoluminescent particles that are directly or indirectly attached to target components.

The invention also comprises a method for the detection of magnetic particles in a sample chamber, wherein a measurement signal is recorded that depends on the orientation of the particles, and wherein the orientation of the particles is modulated, preferably rotated, by a modulated magnetic field during said recording. The measurement signal may particularly originate from an optical near-surface measurement like the ones that can be made with a carrier and an apparatus of the kind described above. As the measurement signal depends on the orientation of the magnetic particle and as this orientation is modulated, the measurement signal will comprise the same modulation, too. This helps to distinguish the part of the measurement signal that originates from the magnetic particles from other parts (i.e. from "noise").

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

By using (frustrated) total internal reflection, very small volumes close to a reflection surface can be probed by the associated evanescent waves (a typical value for the evanescent decay length is between 10 and 500 nm, the exact value depending on the refractive indices of the surrounding media and the entrance angle of the incoming light beam with respect to the surface normal). However, given the fact that many bioassays use magnetic beads with a diameter of several hundred nanometers to several microns, only a small part of the bead surface is interacting with the optical field of the evanescent wave in these cases, giving rise to relatively small scattering/absorption cross sections.

An alternative approach is therefore proposed here that allows to probe a shallow volume close to an optical surface, however with volume heights considerably (microns) larger as compared to the evanescent field technique (typically 100 nm). The technique is preferentially used in combination with large (diameter: several hundred nanometers to microns) scattering and/or absorbing beads that can be pulled away from the surface using external forces, for example with super-paramagnetic beads.

Figure 1:
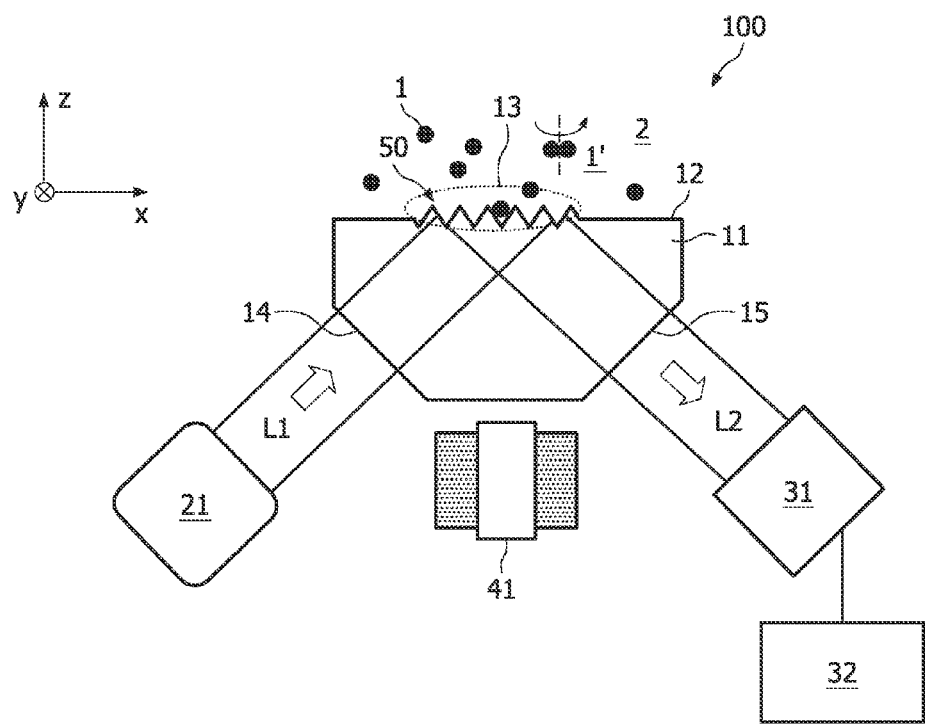
FIG. 1 shows schematically an apparatus with a carrier according to the present invention.

FIG. 1 shows an exemplary realization of this approach with an apparatus 100 according to the present invention. A central component of this apparatus is the carrier 11 that may for example be made from glass or transparent plastic like polystyrene. The carrier 11 is located next to a sample chamber 2 in which a sample fluid with target components to be detected (e.g. drugs, antibodies, DNA, etc.) can be provided. The sample further comprises magnetic particles, for example super-paramagnetic beads, wherein these particles are usually bound as labels to the aforementioned target components. For simplicity only the combination of target components and magnetic particles is shown in the Figure and will be called "target particle" 1 in the following. It should be noted that instead of magnetic particles other label particles, for example electrically charged or photoluminescent particles, could be used as well.

The interface between the carrier 11 and the sample chamber 2 is formed by a surface called "contact surface" 12. This contact surface 12 is optionally coated with capture elements (not shown), e.g. antibodies or proteins, which can specifically bind the target particles. Moreover, the contact surface comprises in an "investigation region" 13 an optical structure 50 that will be explained below.

For the manipulation of magnetic target particles the apparatus 100 may be comprised with a magnetic field generator 41, for example an electromagnet with a coil and a core, for controllably generating a magnetic field at the contact surface 12 and in the adjacent space of the sample chamber 2. With the help of this magnetic field, the target particles 1 can be manipulated, i.e. be magnetized and particularly be moved (if magnetic fields with gradients are used). Thus it is for example possible to attract target particles 1 to the contact surface 12 in order to accelerate their binding to said surface, or to wash unbound target particles away from the contact surface before a measurement. While the Figure shows a single magnetic coil below the carrier, it should be noted that one or more magnetic coils can be disposed at other locations, too.

The apparatus 100 further comprises a light source 21 that generates an input light beam L1 which is transmitted into the carrier 11 through an "entrance window" 14. As light source 21, a laser or an LED, particularly a commercial DVD ($\lambda$=658 nm) laser-diode can be used. A collimator lens may be used to make the input light beam L1 parallel, and a pinhole of e.g. 1 mm diameter may be used to reduce the beam diameter. In general, preferably, the used light beam should be (quasi) monochromatic and (quasi) collimated, as the behavior of the light beam at the various refracting interfaces is strongly dependent on the angle of incidence.

The input light beam L1 impinges onto an investigation region 13 at the contact surface 12 of the carrier 11, where it is refracted into the sample chamber 2 by the optical structure 50. Light of the input light beam that is re-collected from the sample chamber by the optical structure 50 constitutes an output light beam L2.

The output light beam L2 propagates through the carrier 11, leaves it through another surface ("exit window" 15), and is detected by a light detector 31. The light detector 31 determines the amount of light of the output light beam L2 (e.g. expressed by the light intensity of this light beam in the whole spectrum or a certain part of the spectrum). The measured sensor signals are evaluated and optionally monitored over an observation period by an evaluation and recording module 32 that is coupled to the detector 31. An additional lens may be used between exit window 15 and detector 31 for imaging the investigation region 13 onto the detector 31, that optionally can be a 2-dimensional CCD or CMOS detector.

It should be noted that the carrier does not necessarily need to have a slanted entrance window 14 and/or exit window 15, as these facets may for example be part of the external (reader) optics. A matching fluid may for example be used to couple in light from an external reader into the disposable cartridge.

It is possible to use the light detector 31 also for the sampling of photoluminescence light emitted by photoluminescent particles 1 which were stimulated by the input light beam L1, wherein this photoluminescence may for example spectrally be discriminated from other light, e.g. light of the input light beam that was not scattered in the sample chamber. Though the following description concentrates on the measurement of non-scattered light, the principles discussed here can mutatis mutandis be applied to the detection of photoluminescence, too. Note that in the case of photoluminescence or direct scattering detection the detector 31 may also be positioned in a direction other than the output light beam L2, e.g. in a direction perpendicular to the substrate interface 12.

Furthermore, it is possible to use the magnetic field generator 41 for an improved detection of at least one magnetic entity (e.g. the particles 1 and/or clusters of such particles) with non-spherical physical and/or chemical properties in the sample chamber 2. The electromagnet 41 is driven in this case such that it generates a modulated magnetic field, preferably a rotating field. This modulated magnetic field will cause a modulation of the orientation of the magnetic entity, which modulates the detection signal (light beam L2) due to the non-spherical property of the entity. The time-dependent properties of the detection signal can then be used to detect the at least one magnetic entity, to discriminate between different types or sizes of magnetic entities, and/or to discriminate between different types of biological bindings.

An advantage of the described modulation technique is that the specificity and sensitivity of detection can be enhanced. For example, the particle orientation may be modulated at a frequency f. The detection signal may then have corresponding components at several frequencies (e.g. at 2f that can be detected using signal processing techniques. Also, the rotation frequency of the magnetic entity can be much lower than the excitation frequency, e.g. due to relaxation properties of the magnetic grains inside the particle.

An example of a non-spherical physical property is an ellipsoidal shape of a magnetic entity, illustrated in the Figure by a two-particle cluster 1' rotating about the z-axis. Of course rotations about other cluster-axes are possible, too.

An example of a non-spherical chemical property is a particle that is non-spherically coated with a chemical moiety. For example, the particle may be non-spherically coated with an optically-active moiety, e.g. a chemiluminescent enzyme or substrate. When the chemiluminescent reaction is enabled while the particle orientation is modulated in a near-surface optical field, the resulting optical signal will also be modulated.

Figure 2:
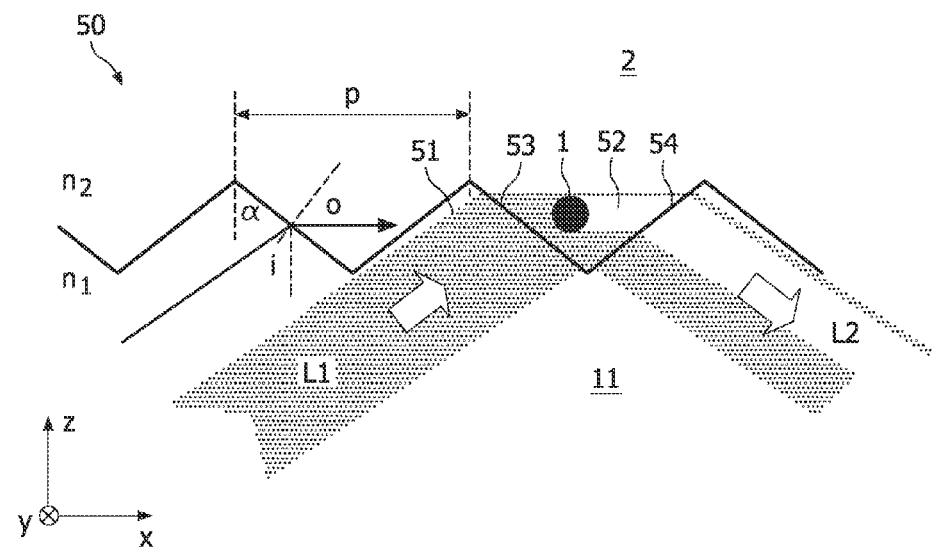
FIG. 2 shows an enlarged view of the optical structure of the carrier of FIG. 1.

An exemplary design of the optical structure 50 on the surface of the transparent carrier 11 is shown in more detail in FIG. 2. This optical structure consists of wedges 51 with a triangular cross section which extend in y-direction, i.e. perpendicular to the drawing plane. The wedges 51 are repeated in a regular pattern in x-direction and encompass between them triangular grooves 52.

When the input light beam L1 (or, more precisely, a sub-beam of the whole input light beam L1) impinges from the carrier side onto an "excitation facet" 53 of a wedge 51, it will be refracted into the adjacent groove 52 of the sample chamber 2. Within the groove 52, the light propagates (substantially parallel to the plane of the contact surface 12) until it impinges onto an oppositely slanted "collection facet" 54 of the neighboring wedge. Here the input light that was not absorbed, scattered, or otherwise lost on its way through the sample chamber 2 is re-collected into the output light beam L2. Obviously the amount of light in the output light beam L2 is inversely correlated to the concentration of target particles 1 in the grooves 52 of the sample chamber.

As a result a thin sheet of light is propagating along the contact surface, wherein the thickness of this sheet is determined by the wedge geometry and the pitch p (distance in x-direction) of the wedges 51. A further advantage of the design is that illumination and detection can both be performed at the non-fluidics side of the carrier.

Given the refractive index $n_1$ of the carrier (e.g. made of plastic), the refractive index $n_2$ of the (bio-)fluid in the sample chamber, and the entrance angle i of the input light beam L1, the wedge geometry can be optimized such that (i) a maximum amount of light is refracted back towards the light detector; and (ii) a maximum surface area is probed by the "reflected" light beam in order to have optimum binding statistics (biochemistry).

In case of a symmetrical wedge structure the refracted ray in the groove 52 between two wedges 51, sensing refractive index $n_2$, should be parallel to the optical interface. With respect to the variables defined in FIG. 2, this means that $o = \alpha$.

Furthermore, in order to have a maximum "clear" aperture for the incoming input light beam, the angle $\alpha$ of the wedge structure should be equal to the entrance angle i of the input light beam:

$i = \alpha$.

Introducing these two demands into the law of refraction, $n_1 \cdot \sin(i - 90° + \alpha) = n_2 \cdot \sin(o)$ implies after some calculations that $$\sin(\alpha) = \frac{n_2}{4n_1} \pm \frac{1}{2} \sqrt{\left(\frac{n_2}{2n_1}\right)^2 + 2}$$

For a plastic substrate with a refractive index $n_1 = 1.6$, and a water-like liquid with a refractive index of $n_2$ somewhere between 1.3 and 1.4, the optimum wedge angle $\alpha$ ranges between about 70° and 74°. An appropriate value for the pitch p of the wedges is about 10 μm, giving a sample volume height of about 1.5 μm.

Figure 3:
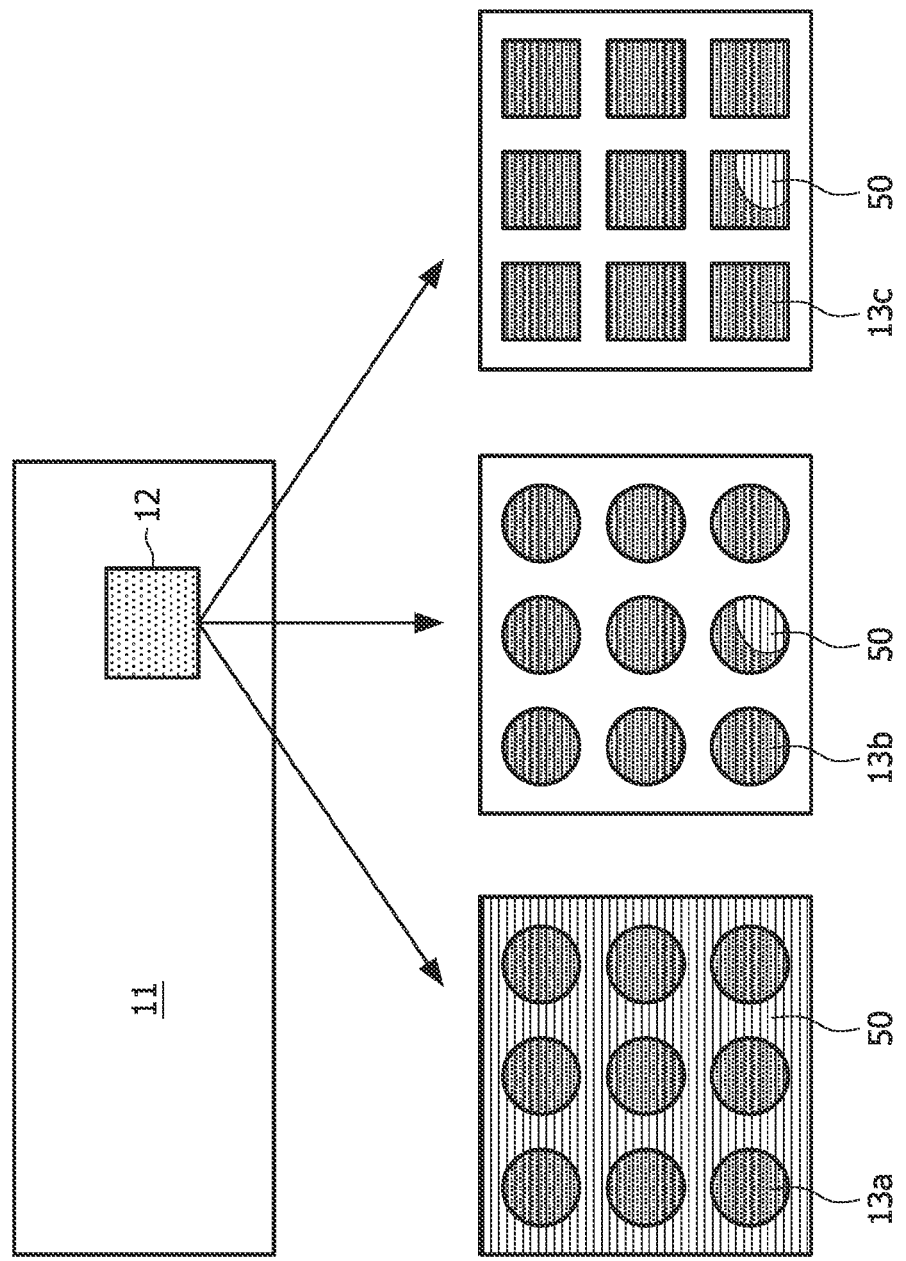
FIG. 3 illustrates several possibilities to combine binding sites with an optical structure.

FIG. 3 shows a top view on a practical realization of the cartridge or carrier 11 with different designs of the contact surface 12. The lower left drawing shows a variant in which the cartridge is equipped with one homogeneous wedge structure 50, on top of which discrete bio-capture probe areas 13a are deposited using printing technology. As an alternative the individual bio-capture probe areas 13b, 13c can be defined by separate wedge-like structures 50, each wedge-like structure not necessarily having the same pitch p, embedded in a optically flat surrounding (e.g. using the injection moulding process), resulting in (geometrically) well-defined capture-probe areas (cf. lower middle and right drawings).

In order to achieve reliable and precise results with a biosensor of the kind shown in FIG. 1 and/or a biosensor using frustrated total internal reflection (FTIR) at a smooth interface, it is important that the sample chamber of the corresponding cartridge is properly filled with the (liquid) sample. This is particularly true if no active transport means are available so that the transport of liquid throughout the cartridge is entirely dependent on capillary filling. It is therefore desirable to have a wetting detector for detecting if the cartridge is filled properly and/or entirely. Preferably, such a wetting detection should be contactless so that no wiring in/to/from the cartridge is needed, adding to robustness and leading to cost reduction.

To address the above issues, a technique for detecting the presence of a fluid in the sample chamber of the cartridge is proposed and explained in the following that may use the main reflection branch in the optical setup of a biosensor for wetting detection. Consequently the same optics as being used for probing the bioassay can be used for wetting detection (e.g. optics that measures FTIR at a smooth contact surface, or optics measuring an output light beam at the optical structures described above). A central idea of such a technique is to use the difference in critical angle at which total internal reflection (TIR) occurs, for the polystyrene-water (in case of wetting) and polystyrene-air (no wetting) interfaces. The refractive optical structure 50 can thus be made such that in the case of no wetting TIR at the refracting interface occurs, whereas in the case of wetting no TIR occurs. In the latter case the light is being transmitted by the polystyrene-water interface and is (partially) captured by the optical structure and redirected ("reflected back") into the cartridge. By carefully tuning the geometry of the optical structure, a kind of "mirroring" retro-"reflector" (however, using refraction instead of reflection) can be made where the light is two times refracted at the carrier-liquid and liquid-carrier interfaces. The design can also be used in a more quantitative manner where the measured signal is a direct measure for the refractive index of the fluid on top of the carrier. The wedge-like optical structure 50 can for example be embossed in a plastic carrier substrate.

Figure 4A:
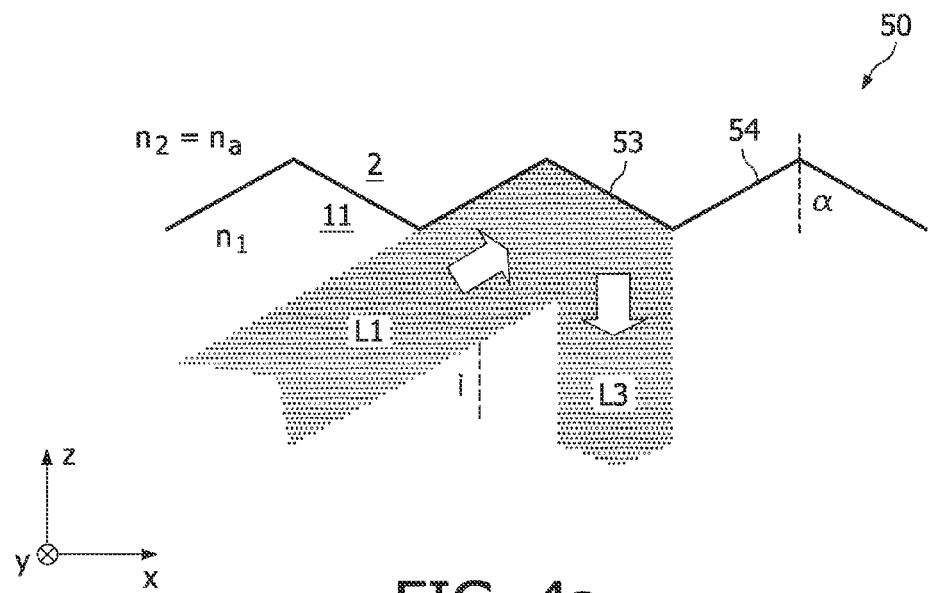
FIG. 4 shows in a view like that of FIG. 2 (*a*) the total internal reflection of an input light beam when the sample chamber is filled with air, and (*b*) the refraction of the input light beam into the sample chamber and the generation of different secondary beams when the sample chamber is filled with a liquid.
Figure 4B:
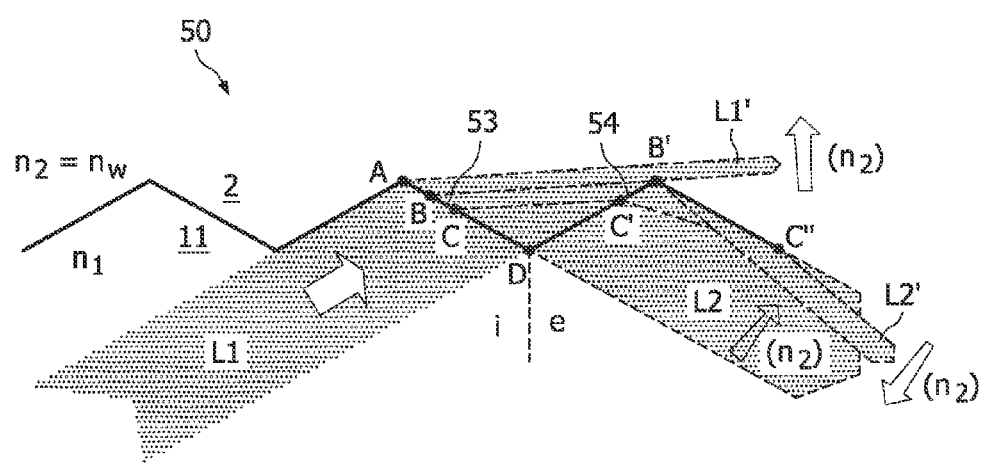

FIG. 4 illustrates (not to scale) the aforementioned concepts in more detail in a drawing similar to that of FIG. 2. FIG. 4a) shows a situation in which the sample chamber 2 is dry, i.e. filled with air having a refractive index $n_a = 1$. FIG. 4b) shows a situation in which the sample chamber 2 is filled with a water-like liquid having a refractive index $n_w$.

The critical angle $\theta_c$ for total internal reflection (TIR) at an optical interface going from high refractive index $n_1$ to low refractive index $n_2$ is given by the relation $\sin(\theta_c) = n_2/n_1$. In case of a polystyrene carrier 11 with refractive index $n_1 = 1.58$ and a water-like fluid with refractive index $n_2 = n_w = 1.33$, the critical angle is $\theta_{cw} = 57.3°$ when the sample chamber is filled with the fluid. If the sample chamber is however filled with air, the critical angle becomes $\theta_{ca} = 39.3°$.

In FIG. 4a), the angle of incidence of the input light beam L1 (with respect to the excitation facet 53) is larger than the critical angle $\theta_{ca}$ for air in the sample chamber 2. Therefore, the input light beam L1 is totally internally reflected at the excitation facet 53 of the optical structure 50 into a TIR light beam L3 propagating under quite a different angle with respect to the surface normal than the input light beam L1.

In FIG. 4b), the sample chamber 2 is filled with a water-like liquid of refractive index $n_w$. The critical angle of TIR is now such that no total internal reflection occurs at the excitation facet 53, but a normal refraction of the input light beam L1 into the sample chamber 2. In the illustrated situation, three different cases can then be distinguished:

1. Input light leaving the excitation facet 53 between points A and B travels past the next wedge and into the sample as a light beam L1'. As indicated by the arrow with index "($n_2$)", the inclination of this light beam L1' (with respect to the horizontal) become steeper and the amount of light in it becomes higher if the refractive index $n_2$ increases.
2. Input light leaving the excitation facet 53 between points B and C is collected between points B' and C' of the collection facet 54 of the neighboring wedge; it is then totally internally reflected between points B' and C" of the excitation facet of this wedge, and leaves the carrier 11 as a secondary component L2' of the total output light. The inclination of this secondary component L2' becomes steeper and its amount of light higher if the refractive index $n_2$ increases.

3. Input light leaving the excitation facet 53 between points C and D is collected between points C' and D of the collection facet 54 of the neighboring wedge; it then propagates without further interference with the optical structure 50 through the carrier 11 as a primary component L2 of the total output light. The inclination of this primary component L2 becomes less steep (more horizontal) and its amount of light lower with increasing refractive index $n_2$.

The Figure shows that only part of the light will be refracted back into the carrier 11 in the case of wetting, resulting in a back-"reflection" efficiency of clearly less than 100%. It should be noted that both the primary output light beam L2 and/or the secondary output light beam L2' can be used as wetting signal.

Not indicated in the Figure is the situation where the incoming angle i is different from the wedge angle α and part of the light is obscured by the rising edge of the optical structure. This light is either propagating into the fluid, or is totally internally reflected hitting surface AD under a slightly offset entrance angle.

The described approach of wetting detection can be used in a biosensor operating like the apparatus 100 of FIG. 1. It can however also be applied in an alternative design of a biosensor which has a smooth surface in an investigation region; in such a biosensor, frustrated total internal reflection (FTIR) can take place at the contact surface, the degree of frustration being a measure for the binding of target components in the investigation region.

In a typical realization of the aforementioned FTIR biosensor, the entrance angle of the input light beam with respect to the normal of the contact surface is fixed at 70°, i.e. sufficiently larger than the critical angle both for a filled and empty cartridge. The FTIR principle comprises monitoring a decrease of intensity of the main TIR-reflected beam, due to scattering and/or absorption of light at bound target particles; consequently, the angle of the detection branch is also making an angle of 70° with respect to the surface normal. Given this geometry, total internal reflection occurs irrespectively of wetting conditions.

However, by providing the carrier (preferably next to or near the FTIR bio-assay probing area) with an optical structure 50 like that of FIG. 4, one can obtain a situation where light is being "reflected" towards the main light detector (e.g. CCD sensor) only in the case of wetting conditions (cf. beams L2, L2' in FIG. 4b). Under the conditions of no wetting, total internal reflection occurs (cf. beam L3 in FIG. 4a) in a direction substantially different from the main FTIR beam, and no light is being reflected towards the main light detector.

For example in case both the wedge angle α and the angle i between input light beam L1 and contact surface normal equal 70°, the input light beam L1 makes an angle of 50° with respect to the excitation facet 53. This is somewhere in the middle of the two critical angles $\theta_{ca}$=39.3° and $\theta_{cw}$=57.3°. When no wetting occurs (FIG. 4a), the incoming beam L1 is therefore totally internal reflected as light beam L3 in a direction such that the FTIR light detector does not see any light (due to the limited collection NA of the detection optics), resulting in a zero (dark) signal. When wetting occurs, the input light beam L1 is transmitted into the fluid and part of the rays being transmitted are again refracted at the rising edge of the refractive optical structure (FIG. 4b).

For given refractive indices $n_1$ and $n_2$, the geometry can be chosen such that the entrance angle i of the input light beam L1 exactly equals the exit angle e of the primary component L2 of the output light beam (cf. considerations with respect to FIG. 2), thereby mimicking the operation principle of a retro-reflector and giving a signal increase (bright) of the FTIR light detector. For a typical configuration with a polystyrene carrier and a water interface this results in a wedge angle α of 74 degrees.

A carrier with an optical structure 50 of the kind described above can for example be manufactured with the help of an aluminum or a NiP insert used in an injection molding process to produce polystyrene cartridges. The necessary structures may be formed in the inserts by a diamond milling process or by 3d focused ion beam (FIB) milling.

Figure 5:
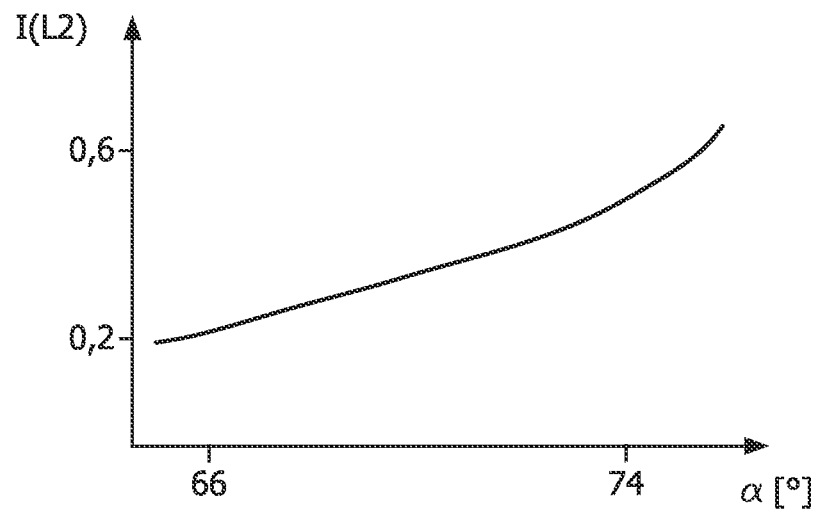
FIGS. 5-9 illustrate the dependency of various parameters on the wedge angle and the refractive index, respectively.
Figure 6:
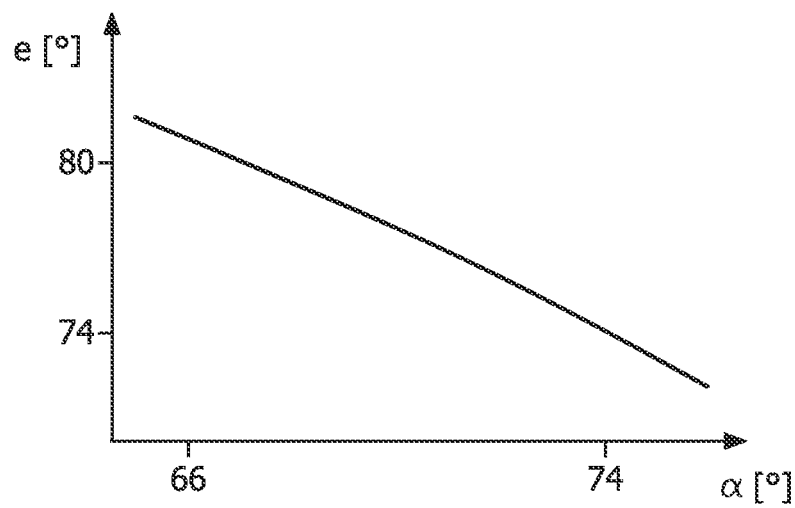

The amount of light in the primary output light beam L2 that is refracted towards a detector under any chosen direction can be optimized by a proper design of the wedge structure 50. The graph in FIG. 5 shows the outcome of a simulation for a wetting structure with polystyrene against water and an entrance angle of i=70°, where the wedge angle α is varied from 65° to 75° (vertical axis: normalized main reflected intensity I(L2)). FIG. 6 shows the corresponding exit angle e of the primary output light beam L2.

Figure 7:
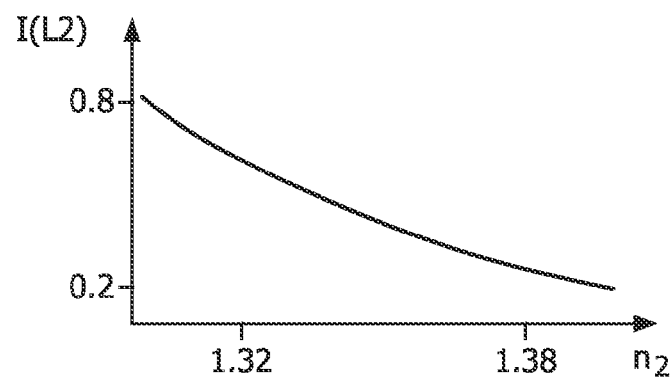
Figure 8:
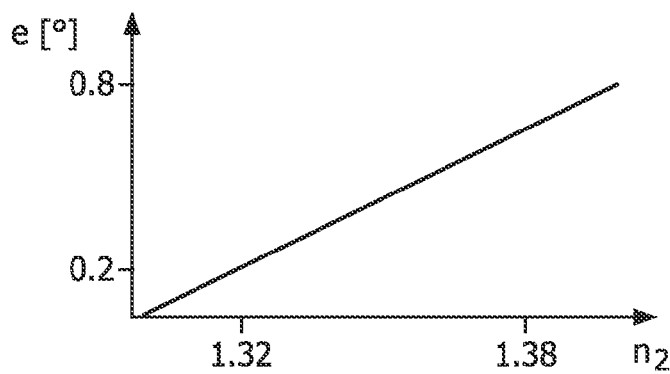
Figure 9:
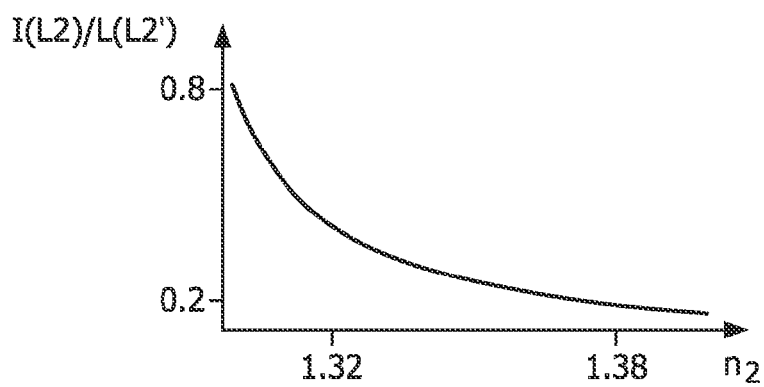

Since the described wetting sensor uses entrance angles close to the critical angle, the refraction angles are very sensitive to changes in refractive index. Consequently the sensor can also be used as a refractive index sensor. FIGS. 7 to 9 show the results of a simulation where the refractive index $n_2$ of the water-like liquid has been varied from 1.3 to 1.4. Several quantities can be used in order to extract the refractive index $n_2$ from the measured signals, for example:

The intensity I(L2) of the primary output light beam L2 (FIG. 7, normalized units on vertical axis).

The angle e of "reflection" of the primary output light beam L2 using e.g. a position sensitive diode (FIG. 8).

The ratio I(L2)/I(L2') of intensities of the primary output light beam L2 and the secondary output light beam L2' (FIG. 9).

In another embodiment the optical structure 50 may be comprised of a regular array of slanted/tilted structures where the slanting angle of the structures (and therefore also the pitch of the grooves) is linearly increased/decreased as a function of their x-position, i.e. along the surface. When the structure is now being imaged onto a 2D-detector or line array, a cutoff in light detection arises at the position where total internal reflection occurs. Given the refractive index $n_1$ of the carrier and the geometry of the optical structure 50, the position of this cutoff (in mm, or detector pixels) is a direct measure for the index of refraction $n_2$ of the medium in the sample chamber.

To be able to detect low analyte concentrations, it is important to obtain as much signal as possible for a single binding event. In the following an approach is described how more magnetic target particles (beads) can be detected for a single binding event. In short, this can be accomplished when a magnetic field with magnetic field lines perpendicular to the sensor surface is applied during the detection and a detection technique is used that has a probing depth of more than one bead diameter. Alternatively, a magnetic field with magnetic field lines parallel to the sensor surface can be used, in which case any surface-sensitive detection technique can be used.

Figure 10:
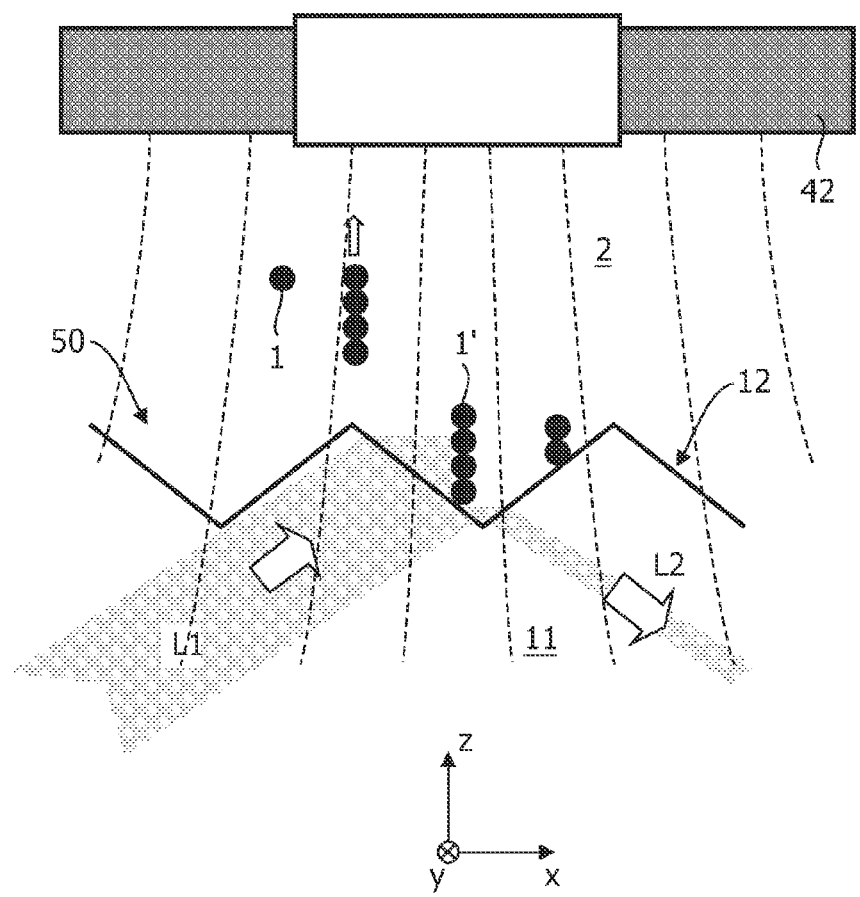
FIG. 10 shows for the optical structure of FIG. 2 the formation of chains or pillars of several magnetic particles.

FIG. 10 illustrates the aforementioned concepts exemplarily for a detection with the optical structure 50 of FIGS. 1 and 2. One of the main advantages of using magnetic target particles 1 is a decrease in the time needed to perform a biological assay that is possible due to magnetic actuation. In a typical procedure, the magnetic particles are actuated to the sensor surface 12, where the number of particles that bind to the surface is dependent on the concentration of an analyte. After this binding step usually a magnetic wash step is incorporated to remove unbound particles from the sensor surface.

The bound particles are then detected using a technique that is sensitive only to particles that are close to the surface.

For the detection of very low analyte concentrations, only very few beads end up on the sensor surface; it is therefore desirable to have a signal that is as large as possible for a single binding event. Instead of trying to increase the signal per bead, the proposed approach aims at obtaining more beads 1 for a single binding event. This is based on the observation that when performing a magnetic wash, the magnetic force generated by a nearby bead (due to the high local field gradient) is much stronger than the magnetic force generated by the washing magnet. If a (normal) single coil is used for the magnetic washing, small pillars 1' pointing towards the top magnet 42 are therefore formed from the bound beads instead of moving all beads towards the magnet.

In a biosensor setup using frustrated total internal reflection (FTIR) detection, the additional beads in the pillars 1' cannot be detected as the evanescent field typically has a depth in the order of 100 nm, whereas a bead diameter is typically in the order of 500 nm. However, using the above double refraction detection (DRD) with the surface structure 50, the probing depth can be increased to detect these additional beads in the pillars 1', resulting in an amplification of the signal.

Figure 11:
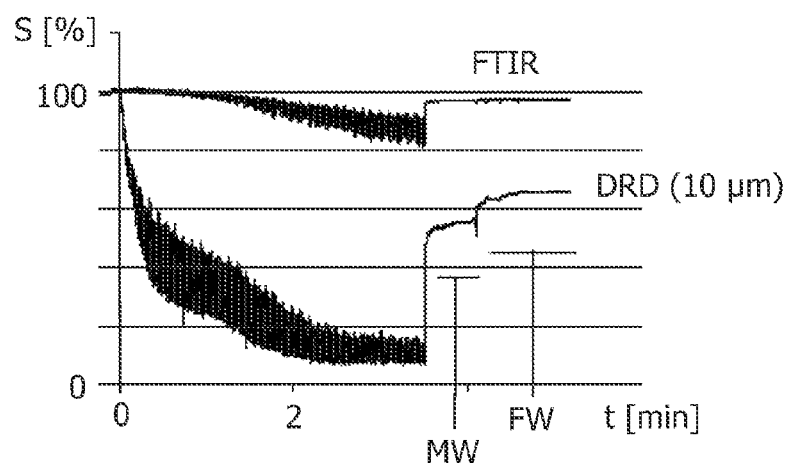
FIG. 11 shows measurement results that demonstrate the difference in endpoint signals when magnetic washing and fluidic washing are used, respectively.

This amplification of the signal S is also evident from FIG. 11, where a typical measurement of a troponin sandwich assay that is concluded with a magnetic wash step (MW) is followed by a fluidic wash step (FW). Two curves are shown corresponding to measurements using frustrated total internal reflection (FTIR) and double refraction detection (DRD), respectively. During the magnetic wash MW, beads form pillars as depicted in FIG. 10 and give rise to an additional signal in the DRD method. During the fluidic wash FW however, these additional beads are removed and only the beads that are bound to the surface remain, resulting in a signal decrease. The signal amplification factor in this particular example is 1.3, i.e. 30% more signal is obtained per bead.

By optimizing the actuation protocol and the DRD structures, still higher amplification factors are possible. For example, a deeper structure (i.e. grooves deeper than 2 μm) would allow the detection of more beads (longer pillars). In addition, the actuation protocol could be optimized to maximize the number of beads close to the surface.

Figure 12:
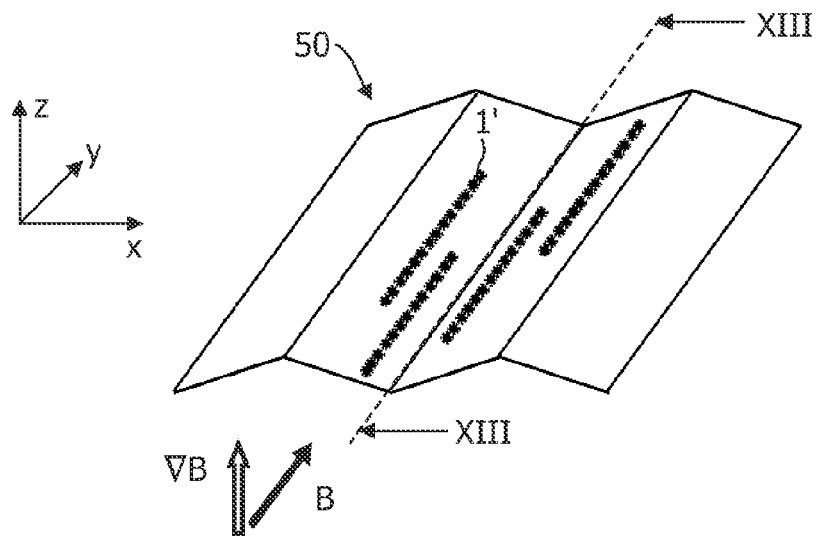
FIG. 12 is a perspective view onto the optical structure of FIG. 1 with chains of magnetic particles lying parallel to the surface.
Figure 13:
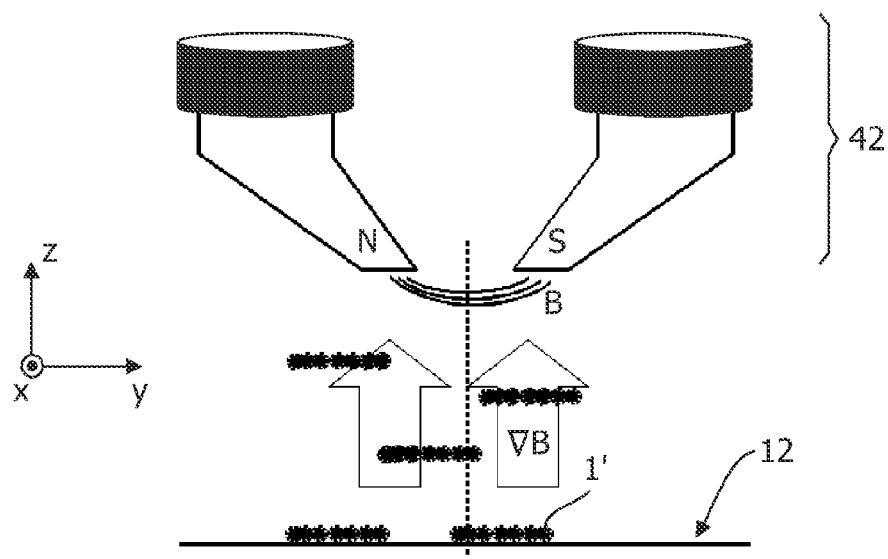
FIG. 13 is a sectional view along the line XIII-XIII of FIG. 12, additionally showing a magnetic field generator.

FIG. 12 illustrates another method to increase the signal amplification by aligning the bead chains 1' parallel to the surface instead of perpendicular. One way to accomplish this is to use a horseshoe setup as top magnet 42 as it is shown in FIG. 13 (not to scale). When the magnet tips have an opposed polarity (north N/south S), the magnetic field lines B run substantially parallel to the sensor surface 12 between both tips, and strings 1' of beads will align in this direction.

Figure 14:
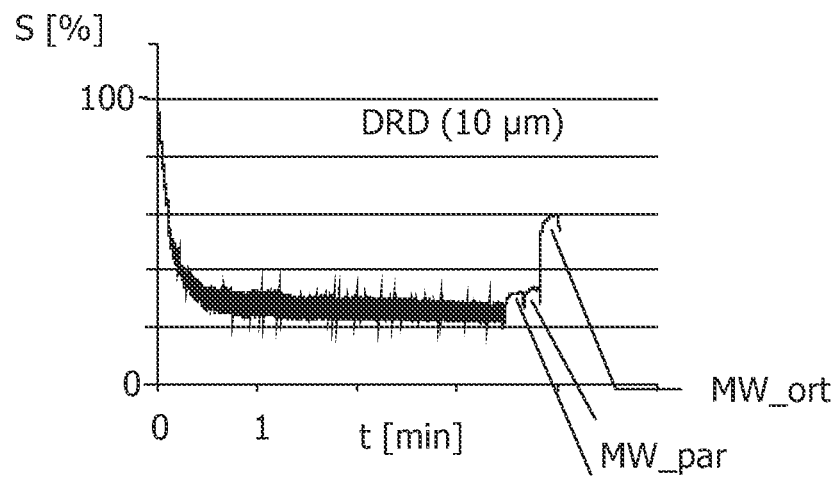
FIG. 14 shows measurement results obtained with the setup that is shown in FIG. 13 when magnetic washing is done with magnetic fields parallel and perpendicular to the surface, respectively.

FIG. 14 shows the difference in signal change between parallel oriented strings and perpendicularly oriented strings on a DRD structure. After an assay in which beads are bound to antibody printed in the DRD structure, a top horseshoe magnet 42 was used in a north-south configuration as a washing step MW_par. During this step, the magnetic field lines are oriented parallel to the surface, but the magnetic field gradient ∇B ensures that the bulk of the beads is moved upwards (as shown in FIGS. 12 and 13). After this first washing step, the top horseshoe magnet 42 was used in a north-north configuration, in which the field lines are oriented orthogonal with respect to the sensor surface (cf. index MW_ort). This results in a large decrease in signal, as some of the beads that were first oriented along the DRD structures are now aligned in strings pointed out of the structures.

Figure 15:
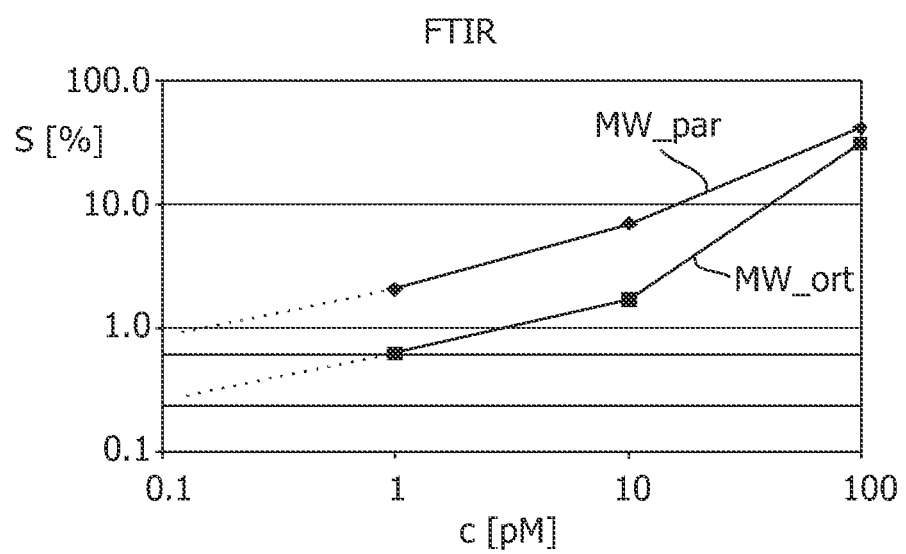
FIG. 15 shows dose response curves for a troponin assay measured with frustrated total internal reflection.

Because in the aforementioned approach multiple beads align parallel and close to the sensor surface, these additional beads cannot only be detected by DRD, but also by other surface detection techniques, for example FTIR detection. FIG. 15 shows dose response curves for a troponin assay, measured by FTIR using a top horseshoe magnet (vertical axis: signal S in relative units; horizontal axis: troponin concentration c). For each measurement, the signal S was determined using a magnetic wash step with either parallel field lines (MW_par) or perpendicular field lines (MW_ort, comparable to the normal magnetic wash with a single top coil). During detection, the strings of magnetic beads were hence oriented parallel to the surface (upper curve) or perpendicular to the surface (lower curve). As can be seen from the diagram, the parallel magnetic signal amplification results in a 3-fold increase in signal compared to the normal detection. The solid horizontal lines that are approached by the dashed lines indicate the measured value for 0 pM troponin.

Figure 16:
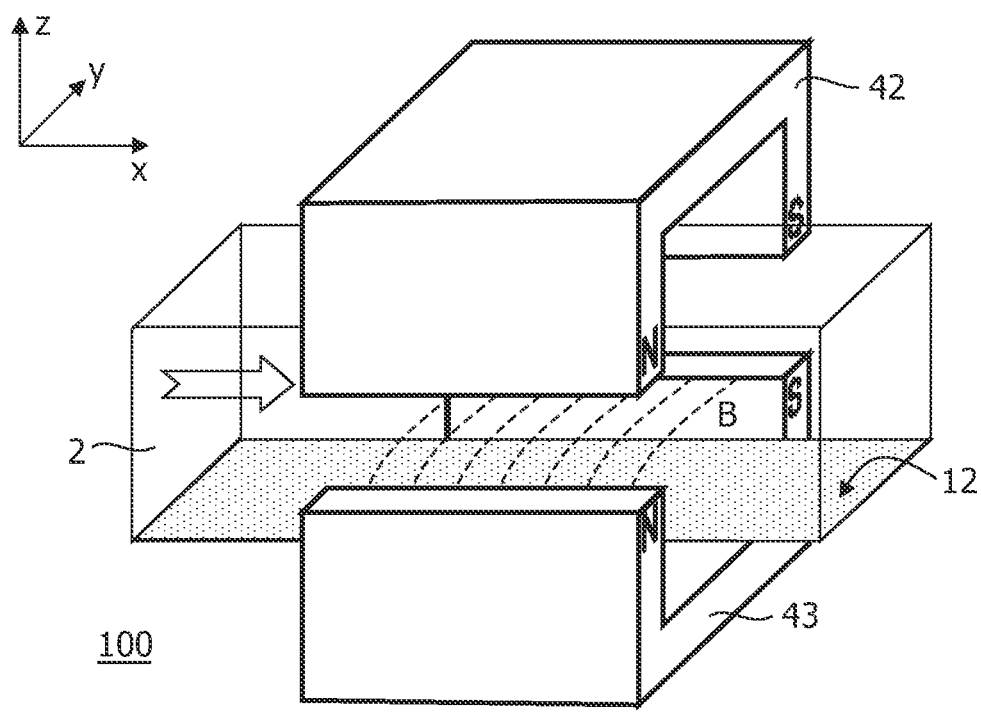
FIG. 16 shows in a schematic perspective view an apparatus according to the present invention in which magnetic poles are disposed on opposite sides of an elongated channel.

FIG. 16 shows in a schematic perspective view an apparatus 100 (not to scale) according to an embodiment of the invention that is particularly suited in combination with a sample chamber 2 having an elongated shape. In the shown example, the elongated shape is due to the fact that the sample chamber 2 is a fluidic channel through which a fluid sample can flow (cf. arrow) in x-direction. The sample chamber 2 comprises a bottom surface 12 at which target particles can be detected e.g. by optical or other methods.

The crucial aspect of the shown design is that there is at least one magnetic field generator 42, 43 the poles N, S of which are disposed at opposite long sides of the sample chamber 2. In this way it can be guaranteed that the resulting magnetic field B is most regular (i.e. parallel) within a large area.

The Figure particularly shows a lower magnet 43 and an upper magnet 42 that are designed as horseshoe magnets, wherein the bow that connects their poles extends below and above the sample chamber 2, respectively. Though both magnets will generate magnetic fields that are substantially parallel to the surface 12 within the sample chamber, the gradients of these fields will have opposite directions. In particular, the bottom magnet 43 will generate a magnetic field that attracts magnetic particles to the surface 12, while the gradient of the upper magnet 42 will pull magnetic particles away from the surface 12.

While the invention was described above with reference to particular embodiments, various modifications and extensions are possible, for example:

- Molecular targets often determine the concentration and/or presence of larger moieties, e.g. cells, viruses, or fractions of cells or viruses, tissue extract, etc.
- In addition to molecular assays, also larger moieties can be detected with sensor devices according to the invention, e.g. cells, viruses, or fractions of cells or viruses, tissue extract, etc.
- The detection can occur with or without scanning of the sensor element with respect to the sensor surface.
- Measurement data can be derived as an end-point measurement, as well as by recording signals kinetically or intermittently.
- The particles serving as labels can be detected directly by the sensing method. As well, the particles can be further processed prior to detection. An example of further processing is that materials are added or that the (bio) chemical or physical properties of the label are modified to facilitate detection.
- The device and method can be used with several biochemical assay types, e.g. binding/unbinding assay, sandwich assay, competition assay, displacement assay, enzymatic assay, cluster assay, etc. It is especially suitable for rapid assays with magnetic actuation and for DNA detection because large scale multiplexing is easily possible and different oligos can be spotted via ink jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An apparatus for optical detection in a sample, the apparatus comprising:
    a carrier comprising:
        an entrance surface including a window for receiving an input light,
        an exit surface including a window for outputting an output light,
        a contact surface including an optical structure comprising a plurality of wedges having grooves configured to form a chamber to include the sample, the grooves including:
            excitation facets slanted in a first direction to refract the input light impinging from the entrance surface into the grooves where the input light propagates substantially parallel to a plane of the contact surface adjacent the chamber, and
            collection facets slanted opposite the first direction to simultaneously collect the output light impinging on the optical structure from the chamber, wherein said output light comprises the input light that was not absorbed, scattered, or lost;
    a light source for emitting the input light through the window of the entrance surface of the carrier towards the optical structure.

2. The apparatus according to claim 1, further comprising a magnetic field generator for generating a magnetic field in the chamber, wherein the generated magnetic field is at least one of substantially parallel to the surface of the carrier, is modulated, and is a rotating magnetic field.

3. The apparatus according to claim 1, wherein at least a part of the input light is
    refracted into the chamber when the chamber includes a medium with a refractive index lying in a first interval; and
    not refracted into the chamber by totally internally reflected at the optical structure when the sample chamber includes a medium with a refractive index lying in a second given interval.

4. The apparatus according to claim 1, further comprising a light detector for detecting a characteristic parameter of the output light, wherein the light detector is configured to separately detect components of the output light that differ in the number of times they were at least one of refracted and reflected by the carrier.

5. The apparatus according to claim 4, further comprising an evaluation unit for evaluating the detection signal of the light detector with respect to at least one of:
    an presence of a target component in the chamber,
    an amount of a target component in the chamber,
    a distinction between different media present in the chamber, and
    a refractive index of the medium in the chamber.

6. The apparatus according to claim 1, wherein the chamber has an elongated shape with long and short sides and comprises at least one magnetic field generator with its poles on opposite long sides of the chamber.

7. A carrier for optical detection in a sample, said carrier comprising:
    an entrance surface including a window for receiving an input light;
    an exit surface including an window for outputting an output light;
    a contact surface including an optical structure comprising a plurality of wedges having grooves configured to form a chamber to include the sample, the grooves including:
        excitation facets slanted in a first direction to refract the input light impinging from the entrance surface into the grooves where the input light propagates substantially parallel to a plane of the contact surface adjacent the chamber, and
        collection facets slanted opposite the firs direction to simultaneously collect the output light beam impinging on the optical structure from the chamber, wherein said output light comprises the input light that was not absorbed, scattered, or lost.

8. The carrier according to claim 1, wherein the chamber is configured such that the collected output light passes a distance of less than 1000 μm through the chamber.

9. The carrier according to claim 1, wherein the optical structure comprises at least one excitation-facet and at least one corresponding collection-facet.

10. The carrier according to claim 1, wherein the output light comprises light from a photoluminescent agent stimulated in the chamber by the input light.

11. The carrier according to claim 1, wherein the optical structure comprises at least one groove having a triangular cross section with two oppositely slanted opposing excitation and collection facets.

12. The carrier according to claim 1, wherein the contact surface includes a plurality of isolated investigation regions.

13. The carrier according to claim 1, wherein the optical structure comprises binding sites for target components of a sample.

14. The carrier according to claim 1, wherein the chamber is configured such the collected output light passes a distance of less than 100 μm through the chamber.

15. The carrier according to claim 1, wherein the chamber is configured such that the collected output light passes a distance of less than 10 μm through the chamber.

16. An apparatus for detection of magnetic particles in a sample, the apparatus comprising:
- a carrier comprising:
  - an entrance including a window for receiving an input light,
  - an exit surface including a window for outputting an output light,
  - a contact surface including an optical structure comprising a plurality of wedges having grooves configured to form a chamber to include the sample, the grooves including:
    - excitation facets slanted in a first direction to refract the input light impinging from the entrance surface into the into the grooves where the input light propagated substantially parallel to a plane of the contact surface adjacent to the chamber having magnetic particles; and
    - collection facets slanted opposite the firs direction to simultaneously collect the output light impinging on the optical structure from the chamber, said output light comprises the input light that was not absorbed, scattered, or lost; and
- a magnetic field generator for generating a magnetic field in the chamber that is substantially parallel to the surface of the carrier and for simultaneously exerting a magnetic force on the magnetic particles in the chamber that pulls them away from said surface.

17. A method for the detection of magnetic particles the method comprising the acts of:
- providing a carrier comprising:
  - an entrance surface including a window for receiving an input light,
  - an exit surface including a window for outputting an output light,
  - a contact surface including an optical structure comprising a plurality of wedges having grooves configured to form a chamber to include the sample, the grooves including:
    - excitation facets slanted in a first direction to refract the input light impinging from the entrance surface into the into the grooves where the input light propagates substantially parallel to a plane of the contact surface adjacent the chamber, and
    - collection facets slanted opposite the first direction to simultaneously collect the output light impinging on the optical structure from the chamber, said output light comprises the input light that was not absorbed, scattered, or lost;
- providing a magnetic field generator for generating a magnetic field in the chamber that is substantially parallel to the surface of the carrier and for simultaneously exerting a magnetic force on magnetic particles in the chamber that pulls them away from said surface;
- recording a measurement signal that depends on an orientation of the magnetic particles; and
- modulating the orientation of the magnetic particles by a magnetic field during said recording act.

\* \* \* \* \*